United States Patent
Vegar et al.

(10) Patent No.: US 12,251,617 B2
(45) Date of Patent: Mar. 18, 2025

(54) TECHNOLOGY ADAPTED TO FACILITATE USER-SPECIFIC CALIBRATION OF INSTRUMENTED MOUTHGUARD DEVICES, INCLUDING CALIBRATION METHODS FOR INSTRUMENTED MOUTHGUARD DEVICES

(71) Applicant: HitIQ Limited, South Melbourne (AU)

(72) Inventors: Michael Vegar, Queenscliff (AU); Ben Nizette, Queenscliff (AU)

(73) Assignee: HitIQ Limited, South Melbourne (AU)

( * ) Notice: Subject to any disclaimer, the term of this patent is extended or adjusted under 35 U.S.C. 154(b) by 251 days.

(21) Appl. No.: 17/906,047

(22) PCT Filed: Mar. 10, 2021

(86) PCT No.: PCT/AU2021/050209
§ 371 (c)(1),
(2) Date: Sep. 9, 2022

(87) PCT Pub. No.: WO2021/179041
PCT Pub. Date: Sep. 16, 2021

(65) Prior Publication Data
US 2023/0107952 A1    Apr. 6, 2023

(30) Foreign Application Priority Data
Mar. 10, 2020    (AU) .............................. 2020900733

(51) Int. Cl.
*A63B 71/08*    (2006.01)

(52) U.S. Cl.
CPC ........ *A63B 71/085* (2013.01); *A63B 2220/40* (2013.01); *A63B 2220/53* (2013.01); *A63B 2220/803* (2013.01)

(58) Field of Classification Search
CPC ....... A63B 71/085; A63B 71/00; A63B 71/08; A63B 71/088; A63B 2220/40;
(Continued)

(56) References Cited

U.S. PATENT DOCUMENTS

| 10,376,210 B2 | 8/2019 | Paris et al. |
| 2004/0168900 A1 | 9/2004 | Tung |

(Continued)

FOREIGN PATENT DOCUMENTS

WO    2022/099385 A1    5/2022

OTHER PUBLICATIONS

International Search Report for International Application No. PCT/AU2021/050209, mailed May 25, 2021, 5 pages.
(Continued)

*Primary Examiner* — Hai L Nguyen
(74) *Attorney, Agent, or Firm* — TraskBritt

(57) ABSTRACT

Technology is adapted to facilitate user-specific calibration of instrumented mouthguard devices, including calibration methods for instrumented mouthguard devices. For example, this includes processes by which instrumented mouthguards, which include components such as accelerometer modules that enable monitoring of head movements of a mouthguard wearer, are calibrated for use by specific individuals. While some embodiments will be described herein with particular reference to those applications, it will be appreciated that the present disclosure is not limited to such a field of use, and is applicable in broader contexts.

25 Claims, 11 Drawing Sheets

(58) Field of Classification Search
CPC ............ A63B 2220/51; A63B 2220/53; A63B 2220/803; A61B 5/11; A61B 5/682; A61B 5/0062; A61B 5/0064; A61B 2562/2019; A61B 2560/0462
See application file for complete search history.

(56) References Cited

U.S. PATENT DOCUMENTS

| | | |
|---|---|---|
| 2016/0106346 A1 | 4/2016 | Benzel et al. |
| 2017/0071538 A1 | 3/2017 | Calcano et al. |
| 2019/0105842 A1 | 4/2019 | Dau et al. |
| 2022/0104768 A1* | 4/2022 | Vegar .................. A61B 5/0004 |
| 2022/0280859 A1* | 9/2022 | Vegar .................. A61B 5/682 |
| 2023/0008811 A1* | 1/2023 | Vegar .................. A61B 5/1121 |

OTHER PUBLICATIONS

International Written Opinion for International Application No. PCT/AU2021/050209, mailed May 25, 2021, 4 pages.

* cited by examiner

TECHNOLOGY ADAPTED TO FACILITATE USER-SPECIFIC CALIBRATION OF INSTRUMENTED MOUTHGUARD DEVICES, INCLUDING CALIBRATION METHODS FOR INSTRUMENTED MOUTHGUARD DEVICES

CROSS-REFERENCE TO RELATED APPLICATIONS

This application is a national phase entry under 35 U.S.C. § 371 of International Patent Application PCT/AU2021/050209, filed Mar. 10, 2021, designating the United States of America and published as International Patent Publication WO 2021/179041 A1 on Sep. 16, 2021, which claims the benefit under Article 8 of the Patent Cooperation Treaty to Australian Patent Application Serial No. 2020900733, filed Mar. 10, 2020.

TECHNICAL FIELD

The present disclosure relates, in various embodiments, to technology adapted to facilitate user-specific calibration of instrumented mouthguard devices, including calibration methods for instrumented mouthguard devices. For example, this includes processes by which instrumented mouthguards, which include components such as accelerometer modules that enable monitoring of head movements of a mouthguard wearer, are calibrated for use by specific individuals. While some embodiments will be described herein with particular reference to those applications, it will be appreciated that the present disclosure is not limited to such a field of use, and is applicable in broader contexts.

BACKGROUND

Any discussion of the background art throughout the specification should in no way be considered as an admission that such art is widely known or forms part of common general knowledge in the field.

In recent years, there has been an increasing focus on the effects of concussions and other traumatic brain injuries on participants in contact sports, such as football/rugby disciplines, martial arts, and the like. In response, various parties have explored the possibility of embedding instrumentation into mouthguards, including the likes of accelerometers and gyroscopes, thereby to collect data representative of head movements. However, as these instrumented mouthguards transition from research instruments to broader usage (for example, as consumer devices), there are challenges to be addressed in the context of device/component design and configuration.

BRIEF SUMMARY

It is an object of the present disclosure to overcome or ameliorate at least one of the disadvantages of the prior art, or to provide a useful alternative.

One embodiment provides a method for customizing an instrumented mouthguard device for a subject, which is performable on an instrumented mouthguard formed via the following steps:
  performing a 3D scan of the subject's mouthguard fitting region;
  based on the 3D scan of the subject's mouthguard fitting region, forming a mouthguard body from resilient plastics material;
  mounting a plurality of motion sensor components to the formed mouthguard body, and performing additional construction steps thereby to form an instrumented mouthguard, such that the positions and orientations of the motion sensor components are uniquely defined based on the unique shape of the subject's mouthguard fitting region;
  the method including:
  performing controlled sample collection processes thereby to identify relative orientation and position of the plurality of motion sensing components;
  performing a 3D scan of subject's head;
  based on (A) the 3D scan of the subject's head; and (B) the relative orientation and position of the plurality of motion sensing components, determining relationships between the relative orientation and position of the plurality of motion sensing components and a defined location in the subject's head.

One embodiment provides a method for customizing an instrumented mouthguard device for a subject, which is performable on an instrumented mouthguard formed via the following steps:
  performing a 3D scan of the subject's mouthguard fitting region;
  based on the 3D scan of the subject's mouthguard fitting region, forming a mouthguard body from resilient plastics material;
  mounting a plurality of motion sensor components to the formed mouthguard body, and performing additional construction steps thereby to form an instrumented mouthguard;
  the method including:
  attaching the instrumented mouthguard to a moving unit that is configured to move the instrumented mouthguard in a predefined manner;
  capturing data from the one or more motion sensor components during the movement of the mouthguard in the predefined manner;
  processing the captured data thereby to identify relative orientation and position of the plurality of motion sensing components;
  performing a 3D scan of subject's head;
  based on the 3D scan of the subject's head, estimating relative locations of the subject's jaw and brain;
  based on (A) the estimated relative locations of the subject's jaw and brain; and (B) the relative orientation and position of the plurality of motion sensing components, defining transforms for data received from the motion sensing components that approximate accelerations for a defined point on the user's head.

One embodiment provides an instrumented mouthguard configured via a method as described herein.

One embodiment provides a method of assessing head movement data including: processing data obtained from a mouthguard configured via a method as described herein.

Reference throughout this specification to "one embodiment," "some embodiments" or "an embodiment" means that a particular feature, structure or characteristic described in connection with the embodiment is included in at least one embodiment of the present disclosure. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms "comprising," "comprised of" or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including" or "which includes" or "that includes" as used herein is also an open term that also means including at least the elements/features that follow the term, but not excluding others. Thus, "including" is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the present disclosure will now be described, by way of example only, with reference to the accompanying drawings in which.

DETAILED DESCRIPTION

Figure 1A:
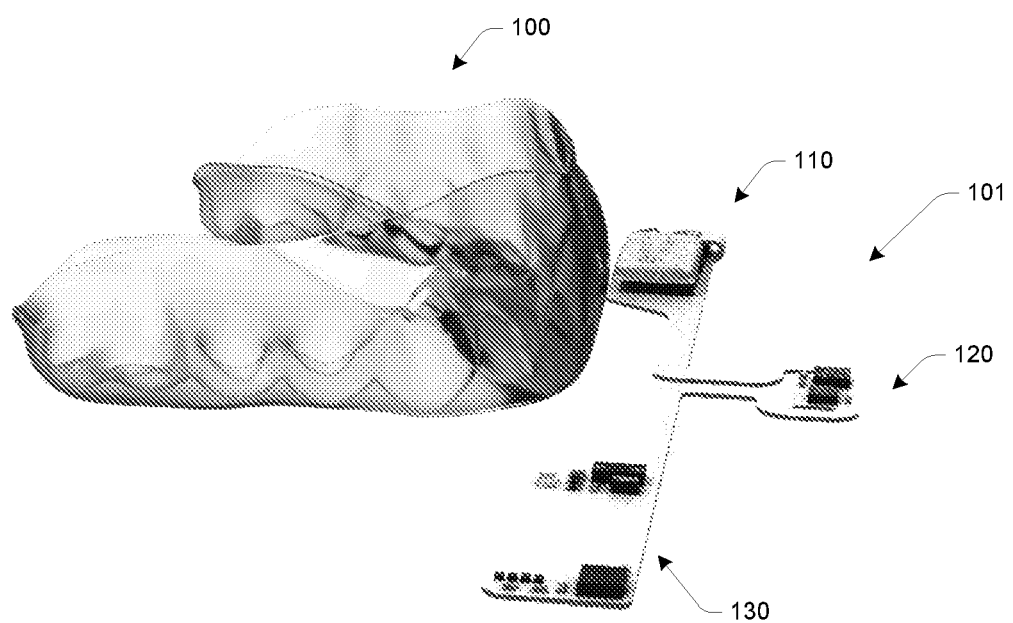
FIGS. 1A-1D illustrate an instrumented mouthguard in varying states of assembly.
Figure 1B:
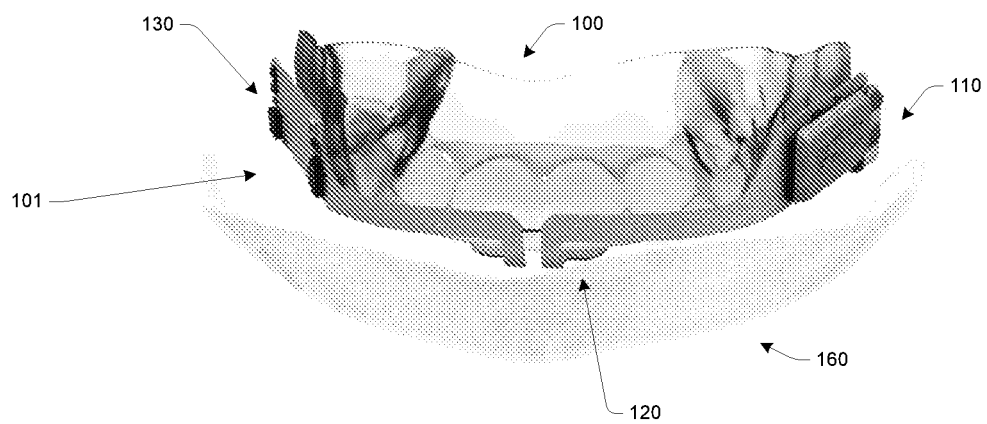
Figure 1C:
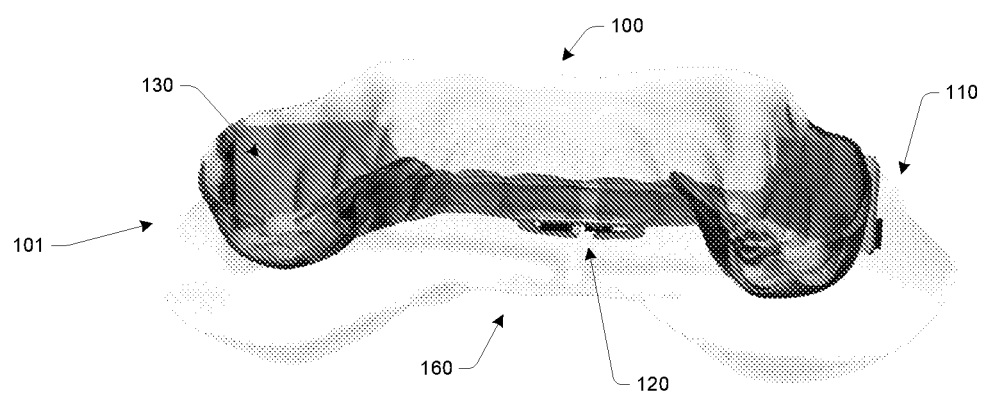
Figure 1D:
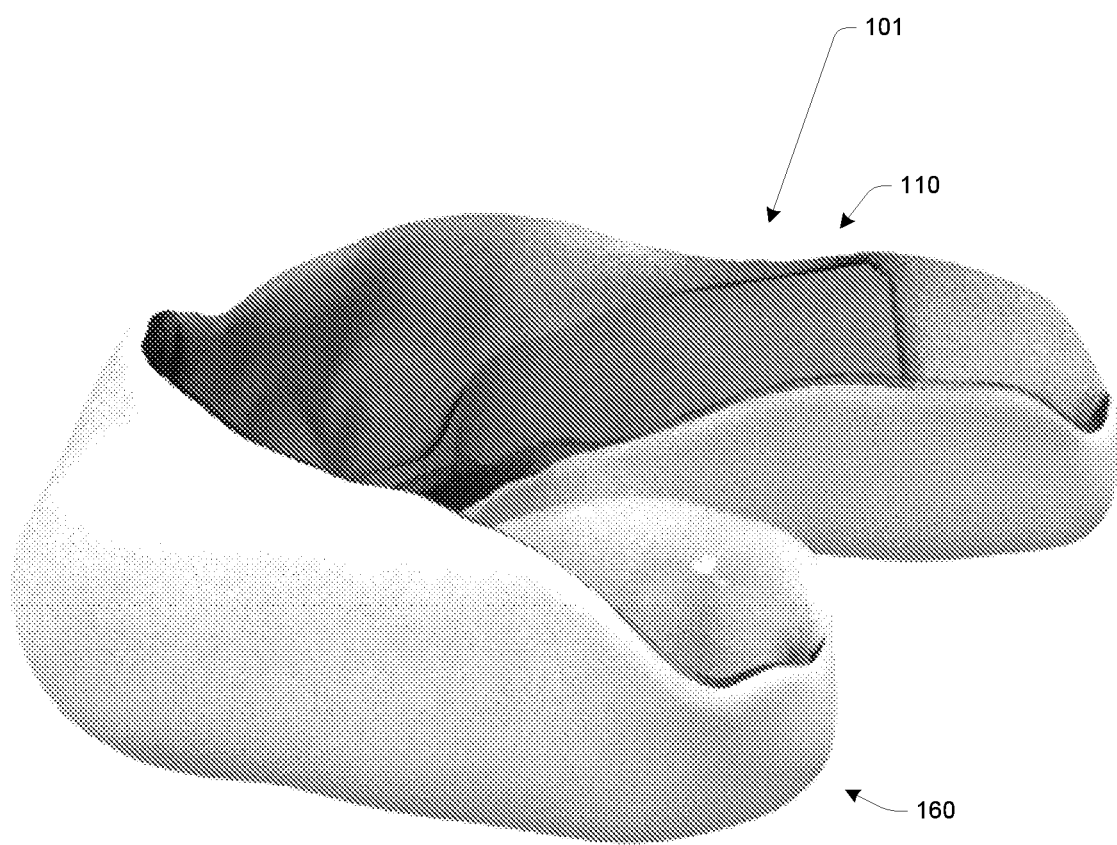

The present disclosure relates, in various embodiments, to technology adapted to facilitate user-specific calibration of instrumented mouthguard devices, including calibration methods for instrumented mouthguard devices. For example, this includes processes by which instrumented mouthguards, which include components such as accelerometer modules that enable monitoring of head movements of a mouthguard wearer, are calibrated for use by specific individuals. While some embodiments will be described herein with particular reference to those applications, it will be appreciated that the present disclosure is not limited to such a field of use, and is applicable in broader contexts.

In overview, embodiments described below include methods for calibration of instrumented mouthguards. It will be appreciated that the shapes and sizes of individuals' mouths and teeth vary significantly across a population (for example, jaw size/shape, teeth size and position, and so on). In this regard, instrumented mouthguard devices are often customized to users, for example, based on use of mouthguard bodies that are shaped based on a 3D scanning and/or molding process. This aspect of customization in some leads to variability in the relative locations and orientations of individual components between instrumented mouthguards. In fact, just as every custom-formed mouthguard is unique, the relative positions and orientations of instrumented components are unique for each mouthguard. Beyond this, different shapes and sizes of user's heads leads to variability of the relative location of instrumented components to a brain center-of-gravity (which is a location of importance in the context of translating instrumented mouthguard motion signals to the motion of the user's head).

In an example embodiment, a method for customizing an instrumented mouthguard device for a subject includes the following steps to form a customized mouthguard:

(i) Performing a 3D scan of the subject's mouthguard fitting region (for example, the teeth and jaw). This is referred to herein as a subject's "dentition scan." Methods for scanning subjects for the purpose of customization of mouthguards are known in the art.

(ii) Based on the dentition scan, forming a mouthguard body from resilient plastics materials. Methods for forming custom mouthguards from dentition scan are known in the art.

(iii) Mounting a plurality of motion sensor components to the formed mouthguard body. For example, the instrumented components may include one or more PCBs, preferably a flexible PCB with a plurality of spaced apart component zones that include respective motion sensor components (for example, accelerometers). For example, this may include accelerometers and gyroscopes. In a preferred embodiment motion sensor component sets are mounted at three spaced apart locations on the mouthguard (for example, front and sides).

(iv) Performing further construction steps thereby to seal the form to an instrumented mouthguard. For example, this may include thermoforming one or more further layers over the instrumented components, thereby to sea those internally of the formed mouthguard.

It will be appreciated that other mouthguard formation techniques may be used. Further examples of mouthguard formation are disclosed in Australian provisional patent application 2020904214, entitled MULTI-LAYERED INSTRUMENTED MOUTHGUARD DEVICES, AND METHODS FOR MANUFACTURING OF INSTRUMENTED MOUTHGUARD DEVICES, which is hereby incorporated by cross reference.

Furthermore, it will be appreciated that configuration/calibration methods described herein a performable on a mouthguard as described above, but are also performable on other instrumented mouthguards (for example, "boil and bite" type mouthguards).

Processes performed on the formed instrumented mouthguard thereby to calibrate motion sensor components, and/or configure the mouthguard such that data from the motion sensors is useful for purposes, for example, assessment of head impacts. These processes may include:

(i) Attaching the instrumented mouthguard to a moving unit that is configured to move the instrumented mouthguard in a predefined manner. For example, this may be a rotating platform that can be caused to rotate at a desired angular velocity about a defined/controlled axis. Preferably the rotating platform has a pre-calibrated IMU (or other components) mounted at a known position (being a known position with respect to the platform and to the mouthguard). It will be appreciated that enables direct knowledge of relative locations of: the mouthguard; the platform; the axis of rotation of the platform; and the IMU mounted to the platform.

(ii) Capturing data from the one or more motion sensor components during the movement of the mouthguard in the predefined manner. Example techniques are discussed in more detail further below.

(iii) Processing the captured data thereby to identify relative orientation and position of the plurality of motion sensing components. For example, this may use optimization methods. Example techniques are discussed in more detail further below.

Then, one or more processes are performed to determine relative position and orientation of the motion sensing components relative to the subject's head. This may include:
(i) Performing a 3D scan of subject's head.
(ii) Based on the 3D scan of the subject's head, estimating relative locations of the subject's jaw and/or brain.
(iii) Based on (A) the estimated relative locations of the subject's jaw and brain; and (B) the relative orientation and position of the plurality of motion sensing components, defining transforms for data received from the motion sensing components that approximate accelerations for a defined point.

For example, the defined point may be the approximate center of mass of the user's brain. However, the defined point (or multiple defined points) may be selected based on a part, depending on reasons for which head movement data is to be processed. In a preferred embodiment, a computation model is configured to assess brain injury and/or concussion risks based on acceleration values for a center of mass for a human brain (or another defined location within the human head).

Example Instrumented Mouthguard

FIGS. 1A-1D illustrate an instrumented mouthguard device according to one embodiment. This provides an example of a mouthguard that may be user customized/calibrated based on technology described here. It should be appreciated that this is an example only, and that the calibration methods may be applied to substantially any instrumented mouthguard devices having motion sensor components (such as accelerometers and/or gyroscopes) at spaced apart locations.

The mouthguard comprises a mouthguard inner body 100, an instrumented component 101, and an outer mouthguard body 160. In the present embodiment, the mouthguard inner body is custom formed based for a user based on a dentition scanning process, such that the mouthguard inner body provides a customized specifically to that user. The instrumented component 101 is then affixed to the inner body, and the outer body 160 sealed to the inner body 100 thereby to sandwich the instrumented component.

Additional details regarding example instrumented mouthguard construction processes are provided in Australian provisional patent application 2020904214, entitled "multi-layered instrumented mouthguard devices, and methods for manufacturing of instrumented mouthguard devices." The disclosure of that application is hereby incorporated by cross reference.

Instrumented component 101 includes a plurality of component zones 110, 120 and 130, which are spaced apart on a flexible PCB that follows a meandering path (i.e., the distance between component zones along the PCB is greater than the direct distance between the component zones).

The meandering path allows for mounting of the flexible circuit board substrate to the mouthguard inner body, such that the component zones are located in a frontal region of the mouthguard body (component zone 120); a side region of the mouthguard inner body (component zone 110); and an opposite side region of the mouthguard inner body from the second component zone (component zone 130). The frontal region is located on an opposite side of a teeth-receiving protective channel to the side region and opposite side region. In this example the frontal region is located on an inner side of the body relative to the protective channel, and the side region and opposite side regions are located on an outer side of the body relative to the protective channel. Outer body member cover 160 is mounted to the body thereby to seal components mounted on both the outer side of the inner body relative to the protective channel thereby to cover and the inner side of the inner body relative to the protective channel.

Figure 2A:
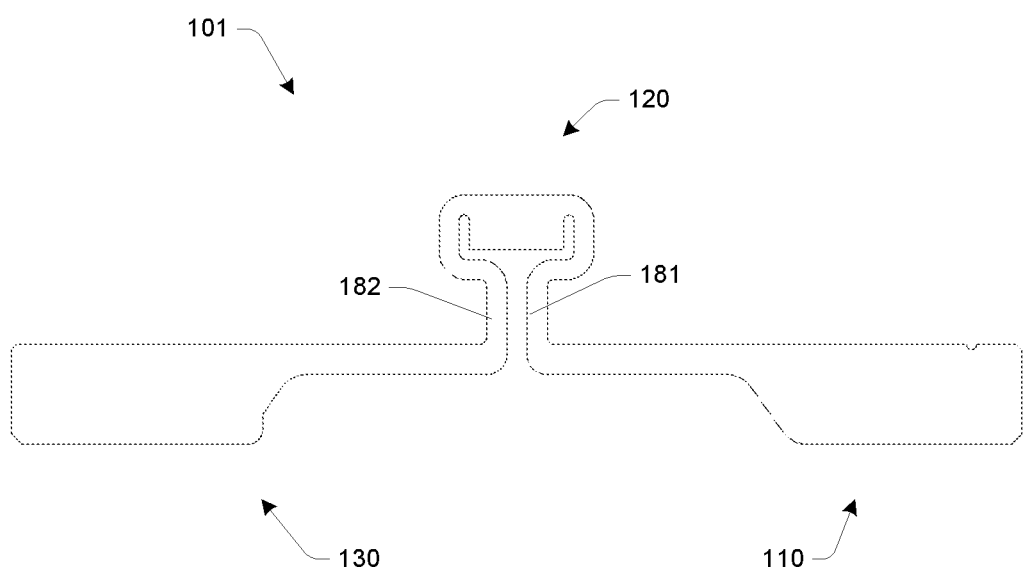
FIGS. 2A and 2B illustrate an example PCB component for an instrumented mouthguard.
Figure 2B:
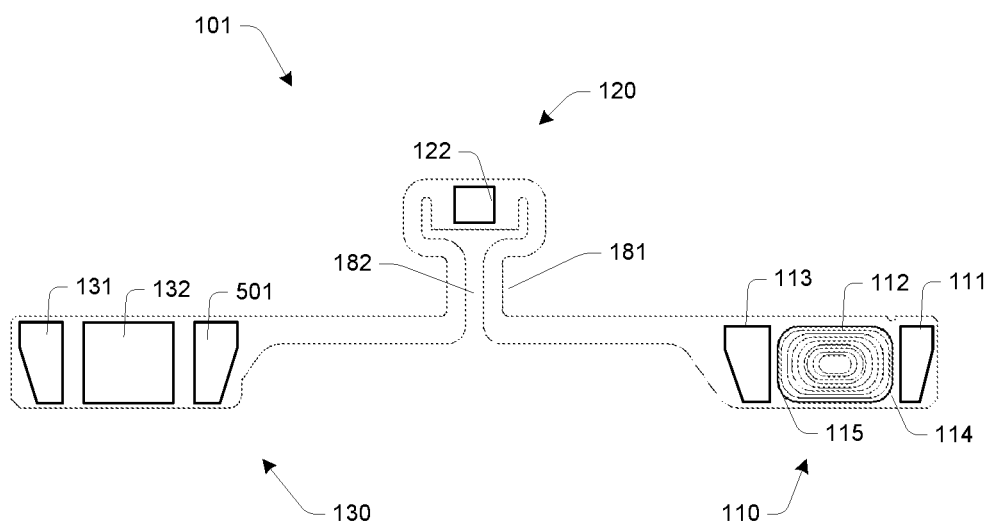

FIGS. 2A and 2B illustrate an instrumented component 101 according to a further embodiment, this being configured for mounting in a mouthguard body thereby to provide an instrumented mouthguard.

As shown in FIG. 2A, component 101 is defined by a flexible circuit board substrate that is configured such that one or more conductive members electronically couples component zones (e.g., printed circuit board regions). The flexible circuit board in this manner defines a conductive member that is irregularly shaped such that it is configured to enable fitting of the component zones at desired locations on mouthguard bodies of varied shapes and sizes. More particularly, a PCB is formed to meander between component zones in a manner that allows for customizable fitting, while providing for added flexibility and robustness when the mouthguard is used. This presents a significant advantage over non-meandering PCBs, or the use of wires interconnecting distinct PCBs.

The PCB substrate illustrated in FIG. 2A may be of variable thickness, and/or have rigidity supports applied, thereby to adjust rigidity on a special basis thereby to protect PCB components as required for robustness.

Component 101 includes three component zones:
A right side component zone 110. In some implementations the right side component zone is configured to support PCB components including an accelerometer (3-axis), wireless communications unit, memory and microprocessor.
A frontal component zone 120. In some implementations, component zone 120 is split provides an accelerometer supporting zone configured to be positioned on the outer side of the front teeth (for a 3-axis accelerometer). In some embodiments the frontal zone additionally includes a low-G accelerometer and/or a gyroscope.
A left side component zone 130. In some implementations the left side component zone provides mounting locations for an accelerometer (3-axis), battery charging unit, and a battery mounting location.
The positioning of components described above, and shown in FIG. 2B, is an example only, and in other embodiments, alternate configurations of components are distributed between the component zones.

A flexible connector member, defined by part of the PCB substrate onto which conductors connects these zones, has a first segment 181 that electronically couples right side component zone 110 and frontal component zone 120, and a second segment 182 that electronically couples frontal component zone 120 and left side component zone 130. As shown in FIG. 2A and 2B, these segments are meandering. In this example, as with examples above, the meandering is such that, segment 181 is greater than the length of the separation of connection points with zones 110 and 120, and segment 182 is greater than the separation of connection points with zones 120 and 130.

The flexible connector member provides a flexible substrate onto which conductive strips and a plurality of PCB components are mounted (for example, PCB components in zones 110, 120 and 130). In some embodiments, the flexible substrate has an increased thickness in certain regions thereby to provide increased rigidity for PCB components that are susceptible to damage as a result of PCB flexion (for example, see regions 111, 112 and 113 discussed below). In some embodiments, additional materials are applied to the flexible substrate thereby to increase rigidity where required.

In the embodiment of FIG. 2B, zone 110 is defined by three substantially rigid PCB regions 111, 112 and 113, interconnected by comparatively flexible regions (flex connectors) 114 and 115. This enables a better fit of zone 110 to a curved surface; in the present embodiment, it is configured to be mounted in a right cheek region of the mouthguard body. Zone 110 includes a range of electronic components, including:

- A 3-axis accelerometer.
- A microprocessor (for example, a Qualcomm CSR1012, or SiLabs BGM13S).
- A memory module (for example, a Macronix MX25L3233).
- A wireless communications module, in this embodiment being a BLUETOOTH® module coupled to a BLUETOOTH® antenna (not shown), for example, an antenna configured to be mounted such that it runs across a frontal region of the mouthguard forward of a wearer's teeth.
- A coupling port to a programming tab (not shown).
- A Light-Emitting Diode configured to be visible through the mouthguard body (not shown), in order to provide a device state indication to a user. For example, this is configured to be positioned behind the wearer's top lip.

It should be appreciated that the variations in rigidity within zone 110 (and across the component generally) is selected based at least in part of PCB components that are to be mounted at the various locations. For example, in one embodiment, one or more of regions 111, 112 and 113 is not rigid, thereby to allow improved curvature upon application to the mouthguard body, and PCB components mounted to the non-rigid region are selected and/or mounted in such a manner to remain robust in spite to flexion in the PCB substrate.

Zone 120 includes a PCB region 122 including a 3-axis accelerometer (which is configured to be mounted to the mouthguard body in a location that in use is positioned behind front teeth). In the present embodiment, PCB region 122 additionally includes a gyroscope, and a second accelerometer that is configured for lower levels of acceleration. Specifically, each component zone includes a 3-axis high-G accelerometer, and one component zone additionally includes a low-G accelerometer.

Zone 130 is configured to be mounted on a left cheek region of the mouthguard body, and includes a PCB that carries a 3-axis accelerometer 131, along with a charging coil 132 to enable wireless charging of a battery unit 151.

In other implementations the battery unit is located in zone 110 or zone 120. In further embodiments, additional components including the likes of gyroscopes may also be present at one or more of the component zones (for example, a gyroscope in combination with an accelerometer at each component zone).

Segment 181 of the conductive member is configured such that, upon mounting to the mouthguard body, it traverses across a bottom region of the mouthguard body at a region approximately adjacent cuspid and first bicuspid (or, alternately, first and second teeth). This allows zone 120 to be provided on an internal region (behind teeth) and zone 110 provided on an external region (in front of teeth). A sealing cover is mounted to the body thereby to seal components mounted on both the outer side of the body relative to the protective channel thereby to cover and the inner side of the body relative to the protective channel.

In a further embodiment, component 101 or a variant thereof is embedded into a post-manufacture customized (e.g., a "boil and bite") mouthguard. In such an embodiment, a standard generic form is injection molded, and a user heats the mouthguard into a temporarily deformable state and bites firmly into it thereby to shape the resilient materials substantially to their teeth before it cools and becomes stable in the new customized shape.

Example Instrumented Mouthguard Customization Methods

Example methods for customizing an instrumented mouthguard device for a subject are described below. In this regard, the term "customization" may include: calibrating motion sensing components; determining relative location and orientation of motion sensing components; determining relative orientation and location of motion sensing components relative to the subject's head; and defining transforms that translate motion data from each of the motion sending components to a define location on the subject's head.

Figure 3A:
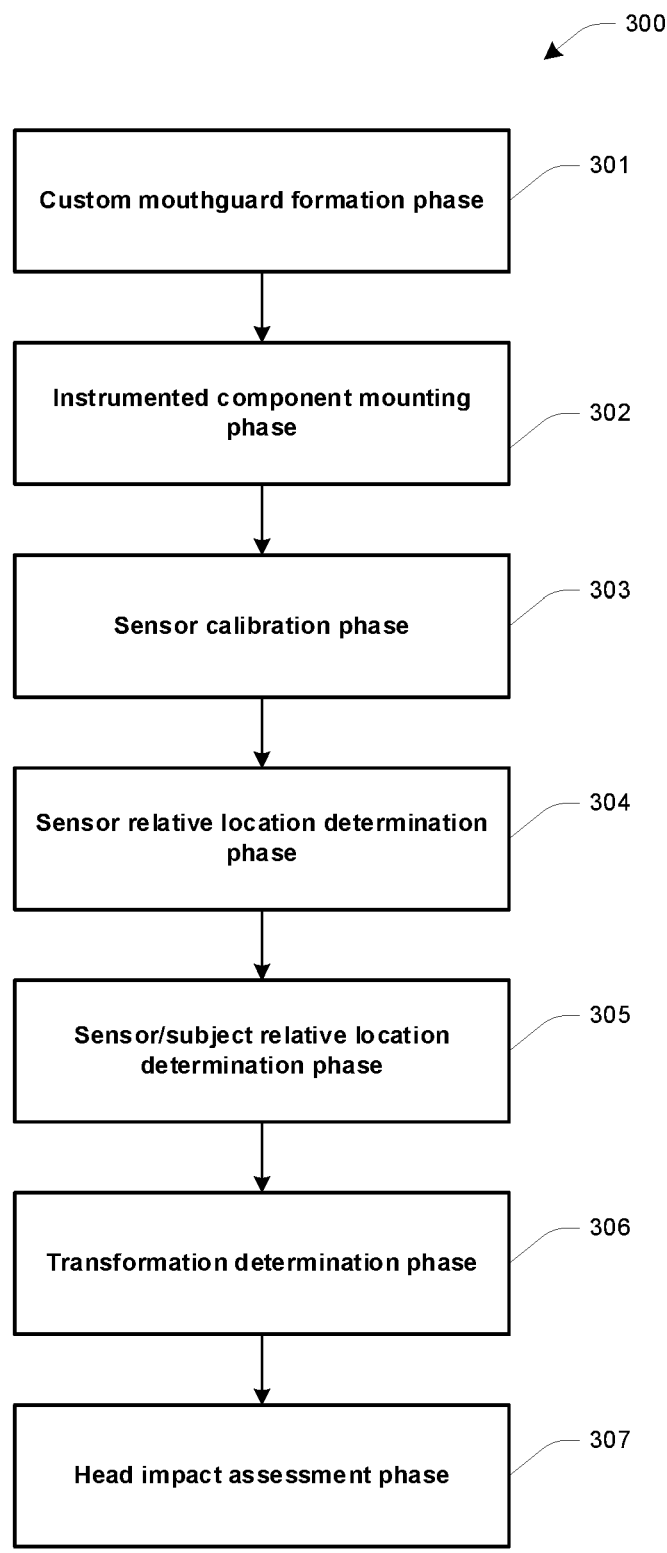
FIGS. 3A-3E illustrate example methods according to embodiments.

FIG. 3A illustrates a method 300 according to one embodiment. This method shows a number of phases relating to customization and operation of an instrumented mouthguard device, from mouthguard body formation to head impact assessment.

Block 301 represents a custom mouthguard body formation phase. This includes processes by which a mouthguard body is customized for a particular subject. For example, this may include 3D scanning of a subject's mouthguard fitting region (teeth and adjacent areas), referred to a dentition scan. This dentition scan is then used to form a mouthguard, for example, by generation of a mold from which a mouthguard body is formed, 3D printing of a mouthguard body, and/or other techniques.

Block 302 represents an instrumented component mounting phase. This includes mounting a plurality of motion sensor components to the formed mouthguard (for example, accelerometers, gyroscopes, and/or IMUs containing accelerometers and gyroscopes), along with other components (for example, a power supply, data transmission module, memory and processor modules, and so on, for example, as discussed further above). These components are mounted, and sealed in place via other construction processes, thereby to form an instrumented mouthguard using the custom mouthguard body from the phase shown in block 301.

It will be appreciated that other mouthguard formation techniques may be used. Furthermore, it will be appreciated that configuration/calibration methods described herein a performable on a mouthguard as described above, but are also performable on other instrumented mouthguards.

For the purposes of examples disclosed herein, it is assumed that the motion sensing components include accelerometers mounted at front and side locations, as shown in the examples discussed further above. In the examples below it is assumed that there is also a gyroscope mounted at least one of those locations. The accelerometer and gyroscope may be separate components, or co-packaged (for example, as an IMU or otherwise).

Block 303 represents a sensor calibration phase. This is used to determine, for accelerometers and gyroscopes, optimal values for some or all of: Offset Vector Gain Vector; and Rotation Matrix.

Figure 3B:
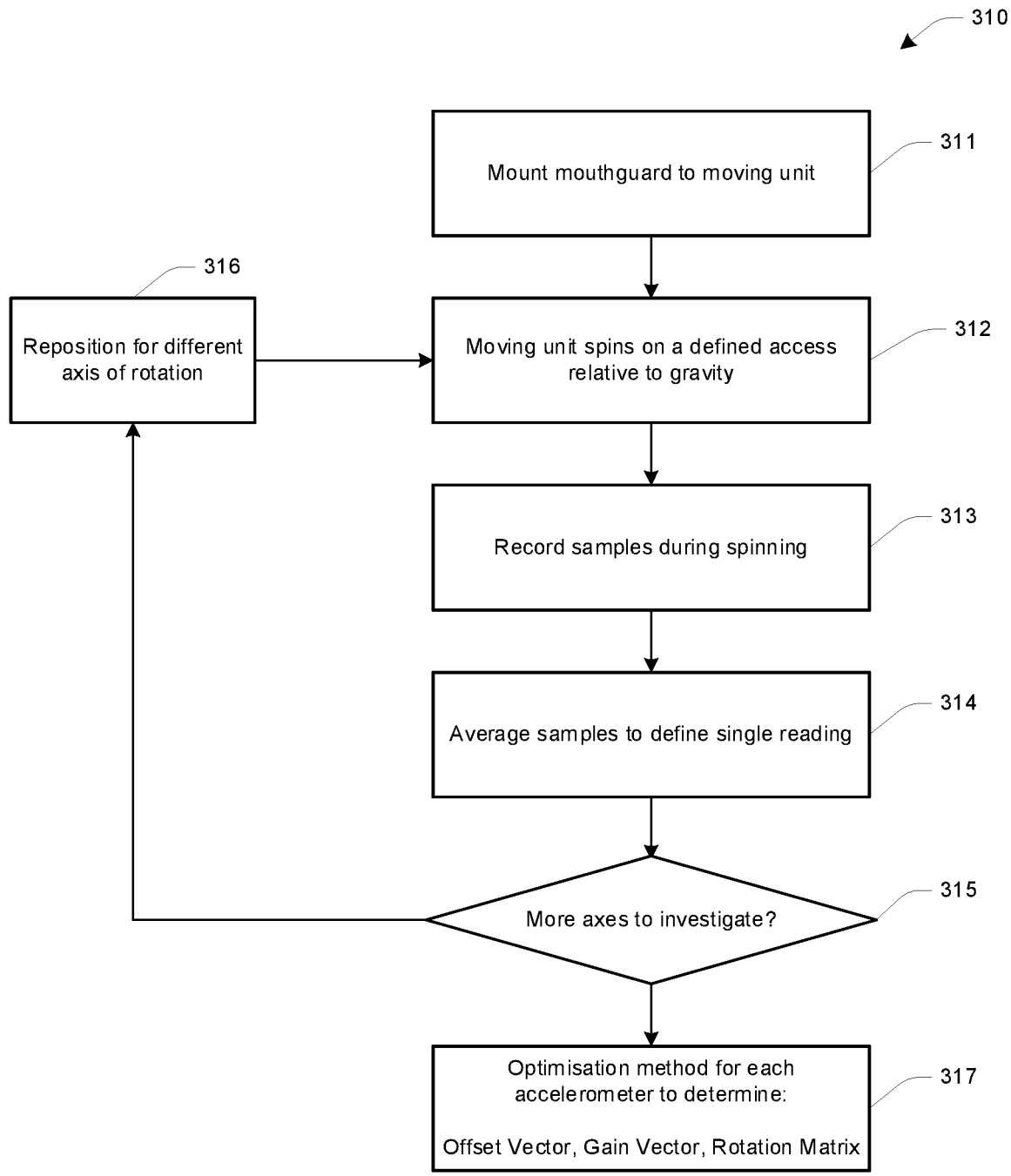

An example method that may form part of the phase shown in block 303 is described by reference to method 310 of FIG. 3B, which illustrates an example process thereby to determine relative orientation, gain and offset for the mounted accelerometers. Block 311 represents a process including mounting the mouthguard to the moving unit, in a defined orientation relative to the moving unit. Then, at block 312 the moving unit is controlled thereby to spin the mouthguard on a defined axis with respect to gravity. The spinning is preferably at a constant angular velocity of between 500 and 5000 revolutions per minute.

Block 313 represents a process including recording samples of a gravity reading from each accelerometer during the spinning. The number of samples should be sufficient to distinguish gravity from noise, for example, several thousand samples. Those samples are then averaged at block 314 thereby to define a single reading for each accelerometer.

As indicated by the decision at block 315, the process of blocks 312 to 314 is repeated for a plurality of varied defined axes, with the mouthguard and/or platform being repositioned/reconfigured for each axis at block 316. This is preferably repeated for nine positions.

Once the readings for each accelerometer have been calculated for the nine axes, an optimization algorithm (for example, a least squares algorithm, or other generic optimization algorithm) is used thereby to determine in respect of each accelerometer optimal values for: Offset Vector; Gain Vector; and Rotation Matrix (block 317). It will be appreciated that there are 9 degrees of freedom for the optimization; hence it is preferable to use the nine different axes when taking recordings.

Figure 3C:
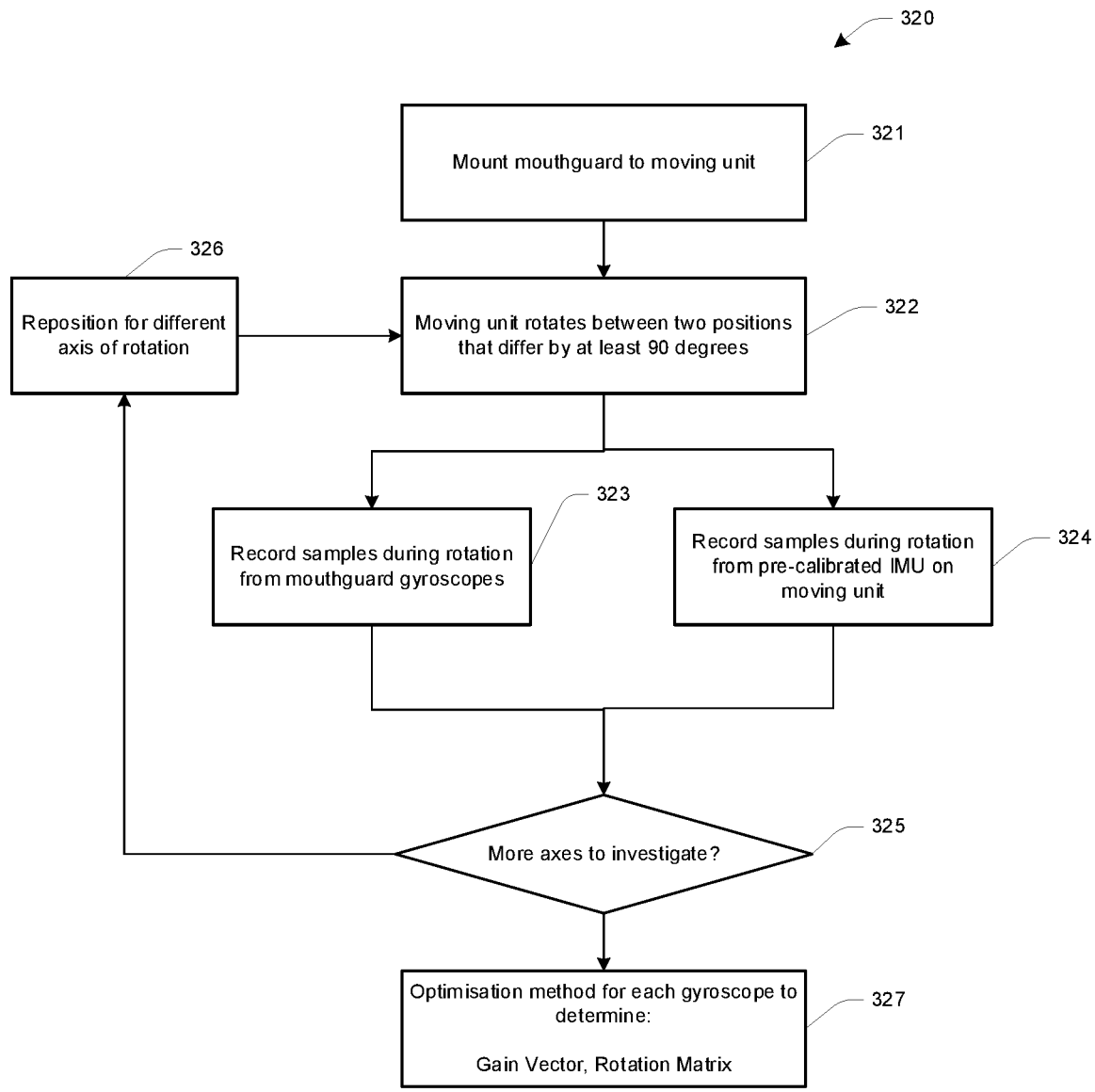

FIG. 3C represents a process performed to determine relative orientation, gain and offset (bias) for one or more gyroscopes. Block 321 represents a process by which the mouthguard is mounted to the moving unit. The moving unit is held stationary, and samples from the gyroscope are recorded, ideally enough samples to distinguish bias from noise (typically several hundred). Those samples are averaged to directly record as bias.

Block 322 represents a process by which the moving unit is rotated between two positions that differ by at least 90 degrees, while recording gyroscope samples. During this rotation, two sets of samples are concurrently recorded:
Samples from the mouthguard gyroscope (or gyroscopes)—see block 323.
Samples from a pre-calibrated IMU mounted to the moving unit at a known location (see block 324).

Preferably, the mounting of the mouthguard to the moving unit is such that the gyroscope is at the axis of rotation, thereby to allow improved measurements and/or simplified computation/processing of samples.

As shown by the decision at block 325 and block 326, the processes of blocks 322 to 324 are repeated for a plurality of axes of rotation. Preferably at least 6 rotational axes are used, covering a diverse range of axes of rotation.

As represented by block 327, an optimization process this then performed to determine Gain Vector and Rotation Matrix for the/each gyroscope. This optionally includes subtracting bias from all gyroscope samples and using a generic optimization algorithm such as Least Squares to find optimal values for Gain Vector and Rotation Matrix (total of Six degrees of freedom) for each gyroscope individually (or for a single gyroscope, where there is only one gyroscope present).

In an alternate embodiment of method 320, a gyroscope is used that can automatically compensate for bias and gain using an internal calibration or self-test mode. This can be used to remove steps related to bias estimation, and reduce the number of required axial iterations due to a corresponding reduction of the number of degrees of freedom of the optimization, from Six to Three.

In a further alternate embodiment, some gyroscopes have a co-packaged accelerometer with well-defined error bounds on the relative orientation of those two sensors. If the accelerometer orientation is calibrated (e.g., as proven in method 310) then this same orientation may be able to be used for the gyroscope. This reduces the number of axial iterations required due to a corresponding reduction of the number of degrees of freedom of the optimization, from Six to Three.

Returning to FIG. 3D, block 304 represents a sensor relative location determination phase. This is performed thereby to determine, for example, relative positions of the accelerometers. An example process is provided in FIG. 3D.

Figure 3D:
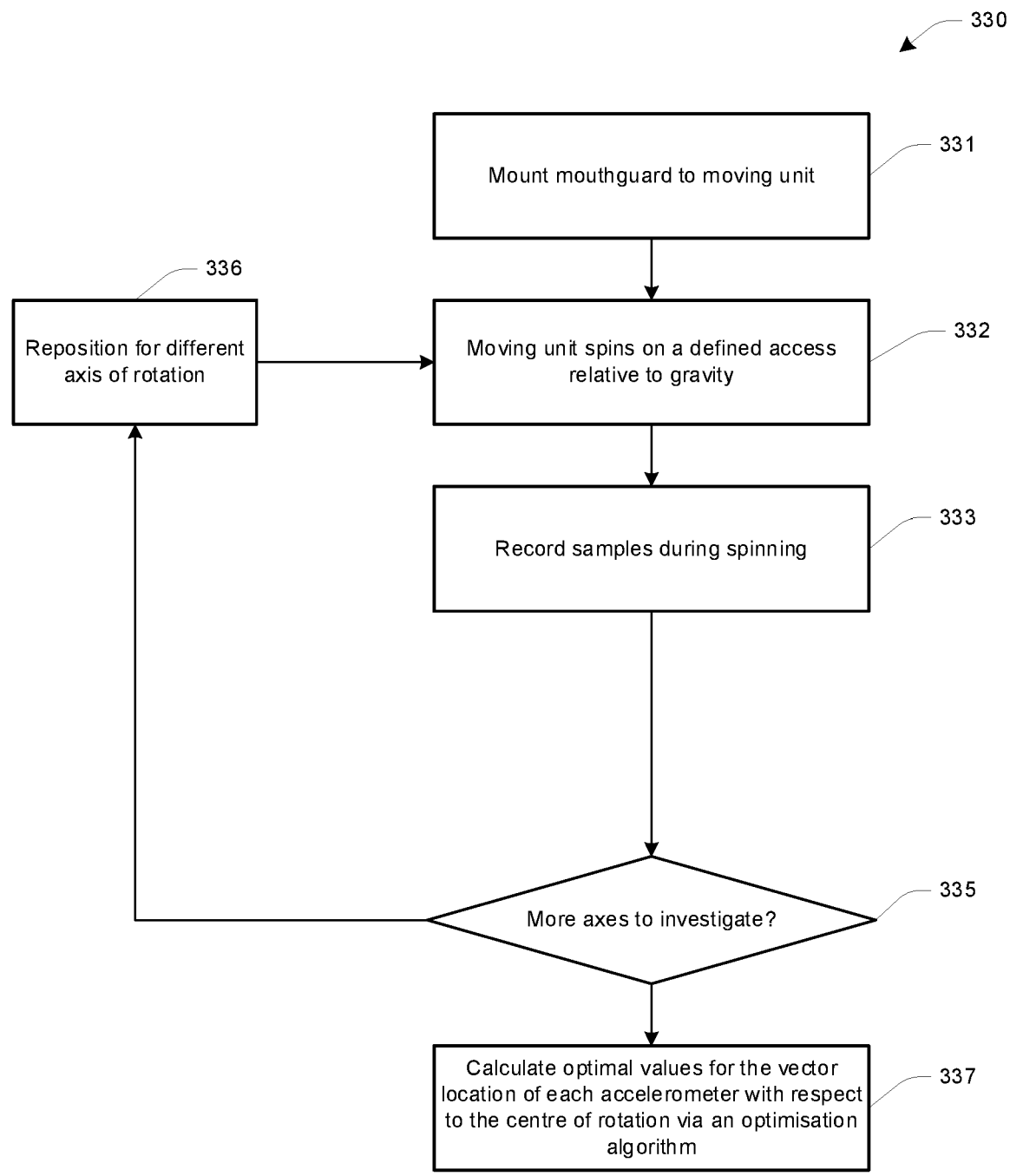

In method 330 of FIG. 3D, the mouthguard is mounted to the moving unit at block 331. Then, as represented by block 332, the moving unit is rotated at high, constant angular velocity, in a defined plane (for example, a plane orthogonal to gravity). Samples are recorded during the rotation (block 333), and these are compensated for offset, gain and rotation (for example, as determined via method 310). Enough samples must be recorded to pick the centripetal acceleration from noise, typically several thousand.

As per the decision at block 335 and block 336, the orientation of the mouthguard relative to the axis of rotation as adjusted and the processes of rotating and sample collection repeated, preferably at least three times covering a diverse range of orientations with respect to the axis of rotation.

Block 337 represents a process whereby an optimization algorithm (for example, a generic optimization algorithm, such as Least Squares) is applied to find optimal values for the vector location of each accelerometer with respect to the center of rotation. In some embodiments, a further step is performed including subtract known offset from the center of rotation to a desired/defined mouthguard coordinate origin.

It is worth noting that the relative location of gyroscopes is not required under the assumption that the mouthguard, when coupled to the teeth, forms a rigid body. Also, as noted, in some embodiments there is only a single gyroscope.

Figure 3E:
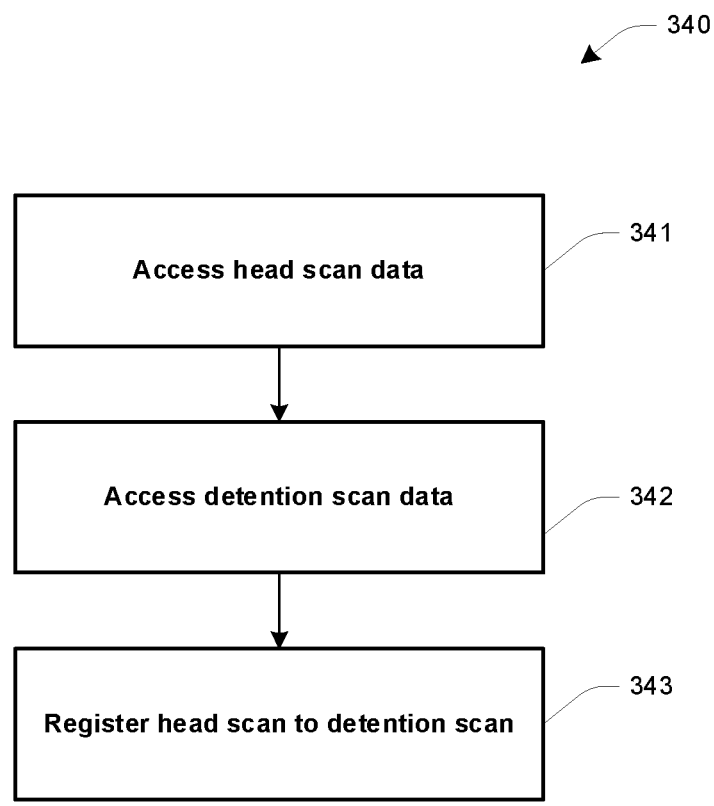

Returning to FIG. 3A, block 305 represents a sensor/subject relative location determination phase, which is used to determine the relative location of mouthguard within head. For example, this is used to determine a spatial relationship between a mouthguard coordinate origin, and the center of mass of the wearer's brain (or an estimation of that position). As shown by method 340 of FIG. 3E, this in essence involves three phases:
Accessing head scan data. A 3D scan is taken of the subject's head. This scan allows for determination of an estimated center of gravity of the brain. See block 341.
Accessing dentition scan data (for the dentition scan used for formation of the mouthguard body). See block 342. The location of the mouthguard coordinate origin is known relative to the dentition scan.

Registering the dentition scan to the head scan. This provides a positional relationship between the mouthguard origin and the center of gravity of the brain.

In some embodiments, the 3D scan of the head is performed with teeth bared. It will be appreciated, however, that it may be challenging for a user to hold a still pose with teeth bared for the duration of 3D scanning of the whole head, unless a particularly fast scanner is used. As such, in some embodiments, whole head scans are taken: a whole head scan in a neutral facial pose, and a localized scan of the mouth and jaw with teeth bared. These can then be combined.

Several techniques for performing the registration process of block 343 are described below:

In some embodiments, the registration process includes using a 3D object manipulation software application to manually register the head and dentition scans using estimates of lip thickness and jaw alignment.

In some embodiments, the registration process includes using a 3D object manipulation software application to manually register the head scan with a bared-teeth scan; then bared-teeth scan with dentition scan.

In some embodiments, the registration process includes using a machine learning model, trained on facial feature data sets, to automatically register head and dentition scans using normative/statistical estimated of lip thickness and jaw alignment.

In some embodiments, the registration process includes using a machine learning model as above to register head scan with bared-teeth scan; then machine learning model or manual process to register bared-teeth scan against dentition scan.

It will be appreciated that the machine leaning models may be trained via performance of preceding manual registration approaches in the first instance.

At this point, the process of FIG. 3A has been performed to a point where information has been generated that defines relative position and/or orientation of the various motion sensors (multiple accelerometers and one or more gyroscopes), and a relationship between those positions/orientations and the subject's head itself. This allows for defining of transforms to a common origin and orientation at the center of mass of the subject's brain, as represented by block 306. This, for example, assists in normalizing acceleration signals from the multiple spaced apart accelerometers to a common orientation and origin, thereby to (for instance) assist in determination of linear and rotational accelerations of the subject's head at the center of gravity. Such data is used for a head impact assessment phase (block 307), which may include analysis of acceleration properties, and/or the use of a model (for example, a FEA model) to predict/model the effect of accelerations on human physiology.

It should be appreciated that in the above description of exemplary embodiments of the present disclosure, various features of the present disclosure are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the present disclosure, and form different embodiments, as would be understood by those skilled in the art. For example, in the following claims, any of the claimed embodiments can be used in any combination.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B that may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the present disclosure, those skilled in the art will recognize that other and further modifications may be made thereto without departing from the spirit of the present disclosure, and it is intended to claim all such changes and modifications as falling within the scope of the present disclosure.

The invention claimed is:

1. A method for customizing an instrumented mouthguard device for a subject, which is performable on an instrumented mouthguard formed via the following steps:
   performing a 3D scan of the subject's mouthguard fitting region;
   based on the 3D scan of the subject's mouthguard fitting region, forming a mouthguard body from resilient plastics material;
   mounting a plurality of motion sensor components to the formed mouthguard body, and
   performing additional construction steps thereby to form the instrumented mouthguard;
   the method including:
   attaching the instrumented mouthguard to a moving unit that is configured to move the instrumented mouthguard in a predefined manner;
   capturing data from the one or more motion sensor components during the movement of the mouthguard in the predefined manner;
   processing the captured data thereby to identify relative orientation and position of the plurality of motion sensing components;
   performing a 3D scan of subject's head;
   based on the 3D scan of the subject's head, estimating relative locations of the subject's jaw and brain; and
   based on (A) the estimated relative locations of the subject's jaw and brain; and (B) the relative orientation and position of the plurality of motion sensing components, defining transforms for data received from the motion sensing components that approximate accelerations for a defined point on the subject's head.

2. The method of claim 1, wherein the plurality of motion sensor components includes a plurality of accelerometers.

3. The method of claim 2, wherein the plurality of accelerometers include: a first accelerometer mounted at a frontal region of the mouthguard; a second accelerometer mounted at a side region of the mouthguard; and a third accelerometer mounted at an opposite side region of the mouthguard.

4. The method of claim 3, wherein the method includes performing a process thereby to determine relative orientation, gain and offset for the mounted accelerometers.

5. The method of claim 4, wherein the process for determining relative orientation, gain and offset for the mounted accelerometers includes:
(i) moving the moving unit thereby to rotate the mouthguard about a defined axis with respect to gravity;
(ii) recording samples of gravity reading from each accelerometer;
(iii) for each accelerometer, averaging the samples to form a single reading, and record that reading in combination with a platform orientation as recorded by a pre-calibrated inertial measurement unit (IMU) that is mounted to the moving unit;
(iv) repeating (i) to (iii) for a plurality of varied defined axes; and
(v) for each accelerometer, using an optimization algorithm thereby to determine optimal values for: Offset Vector; Gain Vector; and Rotation Matrix.

6. The method of claim 5, wherein the optimal values for Offset Vector; Gain Vector; and Rotation Matrix account for a total of nine degrees of freedom.

7. The method of claim 5, wherein the plurality of motion sensor components includes a plurality of gyroscopes.

8. The method of claim 7, further including performing a process for determining relative orientation, gain and offset (bias) for each of the gyroscopes.

9. The method of claim 7, wherein the gyroscopes are configured to autonomously compensate for bias and gain using an internal calibration or self-test mode, and wherein the process for determining relative orientation, gain and offset (bias) for each of the gyroscopes includes:
(i) moving the moving unit between two positions that differ by at least 90 degrees, while recording gyroscope samples;
(ii) simultaneously with (i), recording gyroscope samples from a pre-calibrated IMU mounted to the moving unit;
(vi) repeating (i) and (ii) for a plurality of rotation orientations covering a diverse range of axes of rotation; and
(vii) for each gyroscope, applying an optimization algorithm thereby to determine optimal values for: Gain Vector; and Rotation Matrix.

10. The method of claim 9, wherein the optimal values for Gain Vector; and Rotation Matrix account for a total of three degrees of freedom.

11. The method of claim 9, wherein the plurality of rotation orientations covering a diverse range of axes of rotation include at least three rotation orientations.

12. The method of claim 5, wherein each of the accelerometers is co-packaged with a gyroscope, wherein there are known error bounds on relative orientation of each accelerometer and its co-packaged gyroscope.

13. The method of claim 12, wherein accelerometer orientation is calibrated based on the process for determining relative orientation of claim 5, and wherein a process for determining relative orientation, gain and offset (bias) for each of the gyroscopes includes an optimization algorithm with degrees of freedom reduced based on setting gyroscope orientation based on calibrated accelerometer orientation.

14. The method of claim 1, wherein the plurality of motion sensor components includes a plurality of accelerometers, and wherein the method includes performing a process to determine relative locations of the accelerometers on the mouthguard.

15. The method of claim 14, wherein the process to determine relative locations of the accelerometers on the mouthguard includes:
(i) causing the moving unit to rotate to a high constant angular velocity in a plane orthogonal to gravity;
(ii) recording readings for each of the accelerometers, compensated for offset, gain and rotation;
(iii) repositioning the mouthguard relative to an axis of rotation of the moving unit;
(iv) with the moving unit rotating in the same manner as (i), repeating (ii) and (iii) at least three times, covering a diverse range of orientations with respect to the axis of rotation; and
(v) calculating optimal values for the vector location of each accelerometer with respect to the center of rotation via an optimization algorithm.

16. The method of claim 15, further including: (vi) subtracting a known offset from a known center of rotation to a desired mouthguard coordinate origin.

17. The method of claim 1, further including performing a process to determine a relative location of the mouthguard within the subject's head.

18. The method of claim 17, wherein the process to determine a relative location of the mouthguard within the subject's head includes:
(i) accessing data representative of a 3D scan of the subject's head;
(ii) accessing the 3D scan of the subject's mouthguard fitting region; and
(iii) performing a process to register the 3D scan of the subject's head to the 3D scan of the subject's mouthguard fitting region; region.

19. The method of claim 18, wherein (iii) includes: registering the head and dentition scans using estimates of lip thickness and jaw alignment.

20. The method of claim 18, wherein (iii) includes: registering the 3D scan of the subject's head with a further 3D scan in which the subject's teeth are bared, and registering the further 3D scab to the 3D scan of the subject's mouthguard fitting region.

21. The method of claim 18, wherein (iii) includes: using a machine learning model, trained on facial feature data sets, to automatically register the 3D scan of the subject's head with the 3D scan of the subject's mouthguard fitting region.

22. The method of claim 21, wherein the model uses normative/statistical estimated of lip thickness and jaw alignment.

23. The method of claim 18, wherein (iii) includes: using a machine learning model, trained on facial feature data sets, to automatically register the 3D scan of the subject's head with a further 3D scan in which the subject's teeth are bared, and registering the further 3D scab to the 3D scan of the subject's mouthguard fitting region.

24. The method of claim 18, further including determining relative locations of the motion sending components relative to the subject's brain based on: (A) known relative locations of a plurality the motion sensor components relative to the 3D scan of the subject's mouthguard fitting region; and (B) the process at (iii).

25. A method for customizing an instrumented mouthguard device for a subject, which is performable on an instrumented mouthguard formed via the following steps:
   performing a 3D scan of the subject's mouthguard fitting region;
   based on the 3D scan of the subject's mouthguard fitting region, forming a mouthguard body from resilient plastics material; and
   mounting a plurality of motion sensor components to the formed mouthguard body, and performing additional construction steps thereby to form the instrumented mouthguard, such that the positions and orientations of the motion sensor components are uniquely defined based on the unique shape of the subject's mouthguard fitting region;
   the method including:
   performing controlled sample collection processes thereby to identify relative orientation and position of the plurality of motion sensing components;
   performing a 3D scan of subject's head; and
   based on (A) the 3D scan of the subject's head; and (B) the relative orientation and position of the plurality of motion sensing components, determining relationships between the relative orientation and position of the plurality of motion sensing components and a defined location in the subject's head.

* * * * *